United States Patent
Sahm et al.

[11] Patent Number: 5,987,971
[45] Date of Patent: Nov. 23, 1999

[54] INTERLOCK FOR A STORAGE TANK USED IN CONTAINING A RESPIRABLE LIQUID CRYOGEN

[75] Inventors: Michael K. Sahm, Annendale; David G. Wardle, Bridgewater, both of N.J.

[73] Assignee: The BOC Group, Inc., New Providence, N.J.

[21] Appl. No.: 09/226,729

[22] Filed: Jan. 7, 1999

Related U.S. Application Data

[62] Division of application No. 08/879,230, Jun. 19, 1997.

[51] Int. Cl.[6] ............................. G01N 9/10; F17C 13/02
[52] U.S. Cl. .......................... 73/61.51; 62/49.1; 62/50.7; 73/453
[58] Field of Search .................................. 73/453, 32 R, 73/61.51, 61.44; 62/49.1, 49.2, 50.7; 137/467.5, 487.5

[56] References Cited

U.S. PATENT DOCUMENTS

| | | | |
|---|---|---|---|
| 2,460,503 | 2/1949 | Howe | 73/453 |
| 2,688,868 | 9/1954 | Elkins | 73/453 |
| 3,933,030 | 1/1976 | Forster et al. | 73/32 R |
| 3,964,317 | 6/1976 | Blanchard | 73/453 |
| 4,062,223 | 12/1977 | Lamphere et al. | 62/49.2 |

*Primary Examiner*—John E. Chapman
*Attorney, Agent, or Firm*—David M. Rosenblum; Salvatore P. Pace

[57] ABSTRACT

An sensor for sensing buoyancy force within a liquid mixture stored within a storage tank and an interlock employing the sensor to prevent a respirable cryogenic mixture from being dispensed from the storage tank with an unsafe oxygen content. The sensor has a float adapted to be submerged in the liquid mixture, thereby to exert a buoyancy force referable to the density. The buoyancy force is sensed by a load cell connected to an elongated base element cantilevered from the outlet by a bracket. The mounting of such sensor ensures that the buoyancy force and therefore, the density of the liquid as dispensed will be measured as opposed to liquid density at some other location of the tank. Such sensor can serve in an interlock in which a controller responsive to the load cell and a temperature sensor, also located within the outlet, controls a valve to close the outlet when the mixture has an unsafe oxygen level.

5 Claims, 1 Drawing Sheet

INTERLOCK FOR A STORAGE TANK USED IN CONTAINING A RESPIRABLE LIQUID CRYOGEN

RELATED APPLICATIONS

This is a divisional application of U.S. Ser. No. 08/879,230 filed Jun. 19, 1997 currently allowed.

BACKGROUND OF THE INVENTION

The present invention relates to a buoyancy force sensor for a hydrometer to measure the density of a liquid mixture. More particularly, the present invention relates to such a sensor mounted within an outlet of a storage tank used in storing the liquid mixture. In another aspect, the present invention relates to such a sensor employed in an interlock for the storage tank to prevent dispensing of a respirable liquid cryogen when the liquid contains unsafe levels of oxygen.

The use of hydrometers for determining the density of a mixture is well known in the art. In known hydrometers, a float is provided that exerts a buoyancy force that is dependent upon the density of a mixture. Commonly, the height of the float is observed within a column of a liquid sample to determine the density. In mixtures that by and large contain two components, each of different density, the density measurement will define the component concentration of the mixture. Component concentration of a mixture is important to quantify in order to properly conduct a variety of commercial processes. If density is used for such quantification, the measurement becomes difficult because density can vary within any bulk of mixture to be utilized.

As can be appreciated, where the mixture will come into human contact, component concentration can become especially critical. For instance, cryogenic oxygen and nitrogen mixtures, or liquid air for that matter, are used in a variety of cryogenic processes to ensure that such processes are conducted in a safe, respirable environment. At one extreme, if not enough oxygen is present, the evolved vapors will act as a suffocant. If too much oxygen is present, the resultant atmosphere will be produce highly flammable conditions in the environment. It is a relatively simple matter to ensure that the oxygen concentration is sufficient to support life at the time a container is filled with the respirable mixture. However, since nitrogen is more volatile than oxygen, heat leakage into the container will cause oxygen enrichment of the liquid due to a preferential boil off of nitrogen. Therefore, over time, it becomes difficult to ensure that the liquid being dispensed has not become so enriched in oxygen as to present a fire hazard As will be discussed, the present invention provides a sensor to sense buoyancy force that ensures density will be measured in the liquid as dispensed. Such sensor is particularly useful for service as a sensor for an interlock to prevent the dispensing of a respirable liquid cryogenic mixture if such liquid has an unsafe oxygen level.

SUMMARY OF THE INVENTION

The present invention provides a sensor for sensing buoyancy force within a liquid mixture stored within a storage tank having an outlet. The sensor comprises a float adapted to be submerged in said liquid mixture, thereby to exert a buoyancy force referable to the density of said liquid mixture. An elongated base element is provided and an elastic member is connected to the float and the base element so that the elastic member strains in proportion to said buoyancy force. The elastic member has a load cell attached thereto to register the strain of the elastic member and therefore the buoyancy force. A bracket is connected to said elongated base element and is also configured to wedge said base element into said outlet of said container so as to be cantilevered therefrom. The bracket having an open cross-section to allow said liquid mixture to pass through said outlet. Due to the mounting of the sensor, buoyancy force and therefore, density measurements are conducted at the outlet of the storage tank. Therefore, any density measurement of the liquid will be the density of the liquid as dispensed.

In another aspect, the present invention provides an interlock to prevent the dispensing of a respirable, liquid cryogenic mixture from an outlet of a storage tank if the respirable, liquid cryogenic mixture has an unsafe oxygen content. In this regard, an unsafe oxygen content will be an oxygen concentration by volume above about 22%. Moreover, the ""respirable, liquid cryogenic mixture"" can be either a binary mixture of oxygen and nitrogen or liquid air containing additional components such as argon, carbon dioxide and etc.

The interlock has a float adapted to be submerged in said liquid mixture, thereby to exert a buoyancy force referable to the density of said respirable, liquid cryogenic mixture. An elongated base element is provided and an elastic member is connected to the float and the base element so that the elastic member strains in proportion to the buoyancy force. The elastic member has a load cell attached thereto to register the strain of said elastic member and therefore the buoyancy force. A means is provided for mounting the elongated base element adjacent said outlet and a temperature sensor is located within said outlet for sensing temperature of said respirable, liquid cryogenic mixture. A remotely actuated blocking valve is provided having a closed position for closing said outlet and thereby preventing the dispensing of the respirable, liquid cryogenic mixture with the unsafe oxygen content. A controller responsive to the load cell and the temperature sensor is provided to actuate said remotely actuated valve into its closed position when density of said respirable cryogenic mixture as determined from said buoyancy force and said temperature is indicative of said respirable cryogenic mixture having the unsafe oxygen content. As can be appreciated, the interlock as described above can be employed as a retrofit with a minimum modification to a storage tank.

BRIEF DESCRIPTION OF THE DRAWINGS

While the specification concludes with claims distinctly pointing out the subject matter that applicants regard as their invention, it is believed the invention will be better understood when taken in connection with the accompanying drawings in which:

DETAILED DESCRIPTION

Figure 1:
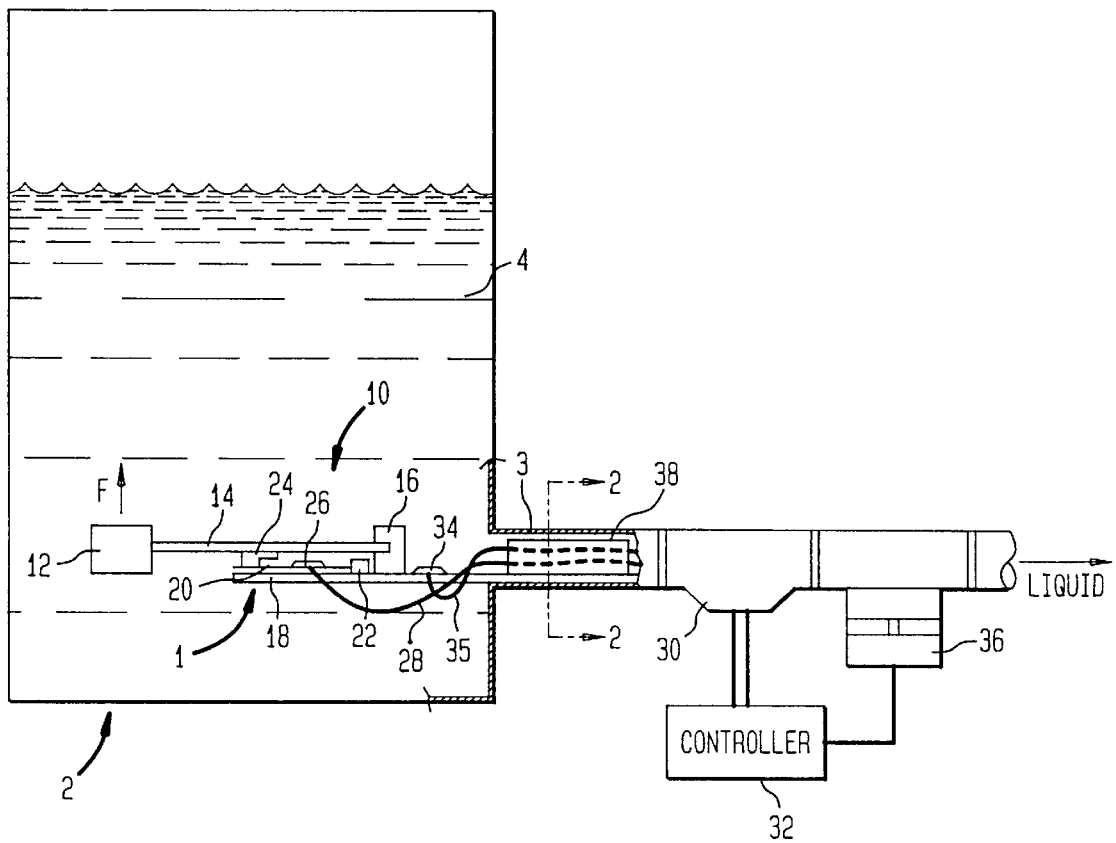
FIG. 1 is a schematic, cross-sectional view of an apparatus in accordance with the present invention installed within a container.
Figure 2:
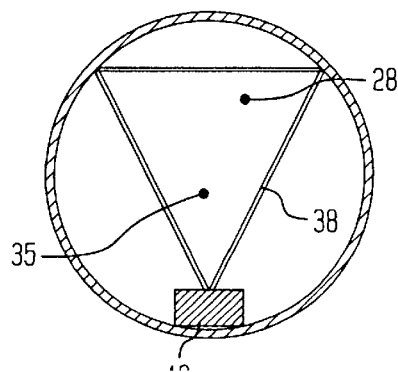
FIG. 2 is a sectional view of FIG. 1 taken along line 2—2 of FIG. 1.

With reference to FIGS. 1 and 2, an apparatus 1 in accordance with the present invention as illustrated as located within a container 2 having an outlet 3 and being filled with a liquid mixture 4 such as a respirable mixture of oxygen and nitrogen or liquefied air. Apparatus 1 includes a sensor 10 provided with a float 12. When float 12 is submerged within liquid 4, it exerts a buoyancy force F that is proportional to the density of liquid mixture 4 at a specific temperature thereof. Float 12 can be a sealed metal or plastic vessel, the material selected to be compatible with fluid 4.

Float 12 is connected to an arm 14 which is in turn connected to pivot 16. Pivot 16 is connected to an elongated base element 18. An elastic member 20, connected between elongated base element 18 and arm 14, can be a metallic strip. Elastic member 20 in the specific illustrated embodiment is connected between a lug 22 of base element 18 and a lug 24 of arm 14. The foregoing arrangement adds leverage to help deflect elastic member 20. Alternatively, an embodiment is possible in which arm 14 is not used so that elastic member 20 has a free, unconstrained end. In such embodiment float 12 is connected to such free end of elastic member 20 to produce flexure thereof.

The deflection of elastic member 20 is proportional to the bouyancy force F and can be sensed by a strain gauge 26 or other load cell. Strain gauge 26 is connected by a conductor 28, passing through a feed through 30, to a controller 32.

The density of liquid mixture 4 can be expressed as a family of linear curves in which each curve is referable to the density of liquid mixture 4 at a specific temperature. In case of a respirable, liquid cryogenic mixture which, by and large contains oxygen and nitrogen, specification of the density of the mixture will also specify its make-up and therefore the oxygen concentration.

In apparatus 1, a temperature sensor 34 is provided to produce a temperature indication of the liquid mixture 4. Temperature sensor 34 is connected to controller 32 by a conductor 35 that also passes through a feed through 30. Controller 32 can be any analog or digital device responsive to strain gauge 26 and temperature sensor 34. In case of a digital device, such as a programmable logic controller, controller 32 is programmed with data representing the above-mentioned family of curves. Since apparatus 1 is designed to function as an interlock for a container of a respirable, cryogenic mixture, controller 32 is also programmed to control a remotely activated valve 36 so that it assumes a closed position to close off outlet 3 when the oxygen content of the liquid is above 22% by volume.

As can be appreciated, apparatus 1 could easily be modified to serve as a hydrometer by utilizing a programmable logic computer having an output of density. In such case, the resulting apparatus might not be used as an interlock in the manner described above and thus, would not include provision for control of a remotely activated valve such as remotely activated valve 36.

Although sensor 10 could be connected to the wall of storage tank 2 near outlet 3, sensor 10 is preferably cantilevered from outlet 3 by provision of a bracket element 38. Bracket element 38 has an open cross-section to allow liquid to pass out of outlet 3. Such cross-section is preferably a triangular-cross section as illustrated. Bracket element 38 is designed with some flex so that elongated base element 18 is wedged within outlet 3. The foregoing arrangement is advantageous because density measurements are constrained to be made at the outlet of storage tank 2. Also, the foregoing arrangement is particularly advantageous from the standpoint of retrofitting storage tanks because its use does not involve modification of storage tanks.

While the present invention has been described with preferred embodiment, as will occur to those skilled in the art, numerous changes, additions and omission may be made without departing from the spirit and scope of the present invention.

We claim:

1. An interlock to prevent the dispensing of a respirable, liquid cryogenic mixture from an outlet of a storage tank if said respirable, liquid cryogenic mixture has an unsafe oxygen content, said interlock comprising:

a float adapted to be submerged in said liquid mixture, thereby to exert a buoyancy force referable to the density of said respirable, liquid cryogenic mixture;

an elongated base element;

an elastic member connected to said float and said base element so that said elastic member strains in proportion to said buoyancy force;

the elastic member having a load cell attached thereto to register the strain of said elastic member and therefore the buoyancy force;

means for mounting said elongated base element adjacent said outlet;

a temperature sensor located within said outlet for sensing temperature of said respirable, liquid cryogenic mixture;

a remotely actuated valve having a closed position for closing said outlet and thereby preventing the dispensing of said respirable, liquid cryogenic mixture with said unsafe oxygen content; and a controller responsive to said load cell and said temperature sensor to actuate said remotely actuated valve into its said closed position when density of said respirable cryogenic mixture as determined from said buoyancy force and said temperature is indicative of said respirable cryogenic mixture having said unsafe oxygen content.

2. The apparatus of claim 1, wherein said mounting means comprises:

a bracket connected to said elongated base element configured to wedge said base element into said outlet of said container so as to be cantilevered therefrom;

the bracket having an open cross-section to allow said liquid mixture to pass through said outlet.

3. The apparatus of claim 1 further comprising:

a pivot connected to said elongated base element;

an arm connecting said float to said pivot so that said buoyancy force tends to rotate said arm about said pivot; and said elastic member is of elongated configuration and is connected at opposite ends to said base element and said arm so that deflection of said arm deflects said elastic member.

4. The apparatus of claim 2, wherein said bracket has an open triangular cross-section.

5. The apparatus of claim 4, further comprising:

a pivot connected to said elongated base element;

an arm connecting said float to said pivot so that said buoyancy force tends to rotate said arm about said pivot; and said elastic member is of elongated configuration and is connected at opposite ends to said base element and said arm so that deflection of said arm deflects said elastic member.

* * * * *